Aug. 27, 1940. G. P. SUNDAY Plant Pat. 418
PEACH TREE
Filed Nov. 27, 1939
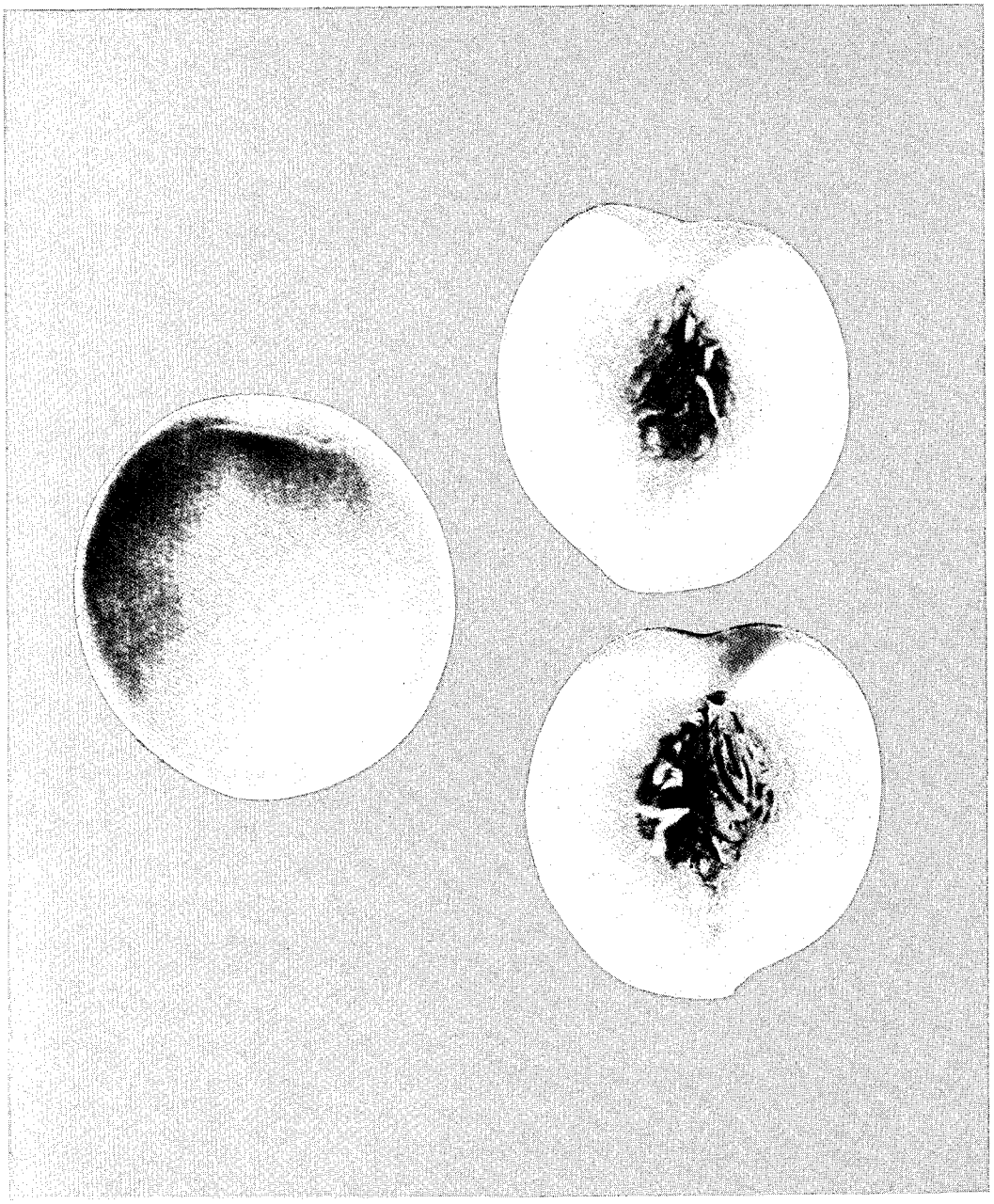
Inventor:-
George P. Sunday
By: Robb & Robb
attorneys.

Patented Aug. 27, 1940

Plant Pat. 418

UNITED STATES PATENT OFFICE

418

PEACH TREE

George P. Sunday, Baroda, Mich., assignor to The Greening Nursery Company, Monroe, Mich., a corporation of Michigan Application November 27, 1939, Serial No. 306,372

1 Claim. (Cl. 47—62)

This discovery appertains to a new and distinct variety of peach tree, originating as a chance seedling, and found by me to have definite, novel and important characteristics which distinguish it from other known varieties of the free-stone class in which this new variety also belongs.

My new variety of peach tree may be said to resemble the J. H. Hale more than it does any other known variety, especially in respect to the large size of the fruit, its firm flesh, bright and attractive yellow and red coloring, with slight, if any, pubescence, excellence of quality and flavor. It is noticeably and definitely different from the J. H. Hale in that whereas Hale has some bitterness around the pit of the fruit, my new variety has no bitterness and is less red in color around the pit.

Also, while the fruit of the J. H. Hale is generally round, that of my new variety is slightly elongated, with the stem end larger and tapering somewhat towards the apex. Moreover, the J. H. Hale is sterile and does not produce its large fruit in very great abundance, while my new variety is self-fertile and a heavy producer of uniformly large peaches.

In habit of growth, my new variety of peach tree is superior to J. H. Hale, in that whereas J. H. Hale is semi-dwarf, spreading and not very hardy, my new variety is vigorous, large, hardy and upright to spreading.

The fruit of the present variety ripens about one week later than the J. H. Hale, grown under comparable conditions, and this characteristic, as well as the other characteristics referred to above, have been tested and found to be fixed, and materially enhance the importance and value of the new variety from a commercial standpoint.

My new variety of peach differs from the variety known as Fertile Hale (Plant Patent No. 175) in essential characteristics of the fruit itself. That is to say, both ground color and cheek are brighter; the flesh is firmer; of finer texture and brighter in color; the skin is smoother, Fertile Hale having more fuzz; and the shape of the Fertile Hale averages rounder than the peaches of this new variety.

The drawing shows on a reduced scale the fruit of my new variety in side elevation and vertical section, and the following is a detail description, all references to color being in accordance with Ridgway's Color Standard and Nomenclature, except where the ordinary dictionary definition is obviously meant:

Tree: Large; vigorous; upright to spreading; open; vase formed; hardy; productive; regular bearer.

*Trunk*—Medium size; smooth.

*Branches*—Medium size; smooth; brown; glossy.

*Lenticels*—Numerous; medium to large in size.

*Leaves*—Length — 7¼ inches; width — 1¾ inches. Large; ovate; acuminate; acutely pointed; medium thickness; medium green; smooth. Margin—Coarsely serrate. Petiole—Medium length; medium thickness. Glands—Average number—three to five; alternate; medium size; mixed, some reniform, others ovate or round; green; position—upper petiole and lower leaf. Stipules—None.

*Flower buds*—Hardy; medium size; medium length; conic; plump; free; pubescent.

Fruit: Maturity when described—Eating ripe about September 9th.

*Size*—Large; diameter axial—2⅝ inches; transverse in suture plane—2⅞ inches; at right angles to suture plane—2⅞ inches.

*Form*—Uniform; symmetrical; conical, toward apex.

*Suture*—Distinct line; has depression beyond pistil point.

*Ventral surface*—Rounded slightly.

*Cavity*—Elongated in suture plane with suture showing on both sides. Depth—½ inch. Breadth—⅝ inch.

*Base*—Cuneate.

*Apex*—Rounded to truncate. Pistil point—apical.

*Stem* — Length — ⅜ inch. Medium size; slightly pubescent. Adherence to stone—strong.

*Skin*—Thick; tough; tenacious to flesh. Tendency to crack—none in wet or dry seasons. Color—Tones of Old Rose, Plate XIII, and Coral Pink, Plate XIII, blending with Flesh Ochre, Plate XIV, and with darker check of deep Corinthian Red, Plate XXVII, and dark Indian Red; check color in fairly equal proportion to remainder of surface. Down—Scant or wanting; short.

*Flesh*—Color—Blending tones from Ochraceous Orange near skin through Ochraceous-buff and light Ochraceous-buff, Plate XV, at pit, where lightest tone is flushed with Carrot Red, Plate XIV. Surface of pit cavity—tones ranging from Chestnut Brown, Plate XIV, Hazel, Plate XIV, Cinnamon-rufous, Plate XIV, Madder Brown, Plate XIII, and Van Dyke Red, Plate XIII. Amygadalin—Wanting. Juice—Moderate, rich. Texture—Firm, fine, melting. Fibres — Fine, tender. Ripens—Even. Flavor—Subacid. Aroma—Distinct. Eating quality—Best.

*Stone*—Free; retains short fibre-like threads along ridges. Size — Medium. Length — 1¾ inches. Breadth—1⅜ inches. Thickness — ¾ inch. Form — Generally oval, pointed toward the apex. Base—Oblique. Hilum—Oblong. Apex—Acuminate. Sides—Unequal, curved on right. Surface —Irregularly furrowed near base, toward apex throughout; ridged near base throughout; pitted toward base throughout. Ridges—Rounded. Pits—Elongated. Ventral edge—Medium thick, without wing toward base throughout. Dorsal edge—Full with deep groove toward base, ridges on either side, interrupted. Color of stone —Tones ranging through Chestnut Brown, Plate XIV, Hazel, Plate XIV, and Cinnamon-rufous, Plate XIV. Tendency to split —None.

*Use*—Market, local, dessert, culinary, canning.

*Keeping quality*—Good.

*Resistance to* — Insects — Good. Diseases — Good.

*Shipping quality*—Good.

Having thus described my new variety, what I claim as new and desire to secure by Letters Patent is:

A new and distinct variety of peach tree characterized as to novelty by its similarity to the J. H. Hale in general details, but having a later ripening period of its fruit, less bitterness and red color around the pit of the fruit, greater abundance of large fruit of slightly elongated and tapering form, more vigorous, greater hardiness, generally large and more upright habit of growth, and its self-fertilizing habit, substantially as shown and described.

GEORGE P. SUNDAY.